(12) United States Patent  
Elmer et al.

(10) Patent No.: US 7,198,049 B2
(45) Date of Patent: Apr. 3, 2007

(54) IMPLEMENT FOR TREATING HAIR AND METHOD OF TREATING HAIR USING THE SAME

(75) Inventors: Simon James Elmer, Twickenham (GB); Philip Davies, Banstead (GB)

(73) Assignee: The Procter & Gamble Company, Cincinnati, OH (US)

( * ) Notice: Subject to any disclaimer, the term of this patent is extended or adjusted under 35 U.S.C. 154(b) by 395 days.

(21) Appl. No.: 10/714,229

(22) Filed: Nov. 14, 2003

(65) Prior Publication Data

US 2004/0216759 A1    Nov. 4, 2004

(30) Foreign Application Priority Data

Nov. 14, 2002   (EP)  .................................. 02257874

(51) Int. Cl.
*A61K 7/13*      (2006.01)
*A54D 19/18*    (2006.01)

(52) U.S. Cl. ....................................... 132/208; 132/270

(58) Field of Classification Search ................ 132/207, 132/208, 209, 221, 222, 270, 212
See application file for complete search history.

(56) References Cited

U.S. PATENT DOCUMENTS

| | | | | | |
|---|---|---|---|---|---|
| 1,884,305 | A | * | 10/1932 | Gentry | ........................ 132/206 |
| 2,655,924 | A | | 10/1953 | Petitta | |
| 2,814,871 | A | | 12/1957 | Childress | |
| 2,819,721 | A | * | 1/1958 | Zakon | ........................ 132/208 |
| 2,839,066 | A | * | 6/1958 | Sanders | ....................... 132/221 |
| 3,255,765 | A | * | 6/1966 | Sturdivant | ................... 132/223 |
| 3,295,535 | A | * | 1/1967 | Amato | ......................... 132/212 |
| 3,610,257 | A | * | 10/1971 | Hall | ............................. 132/270 |
| 3,640,289 | A | | 2/1972 | Sbarra | |
| 3,726,289 | A | * | 4/1973 | Thompson | ................... 132/221 |
| 3,968,805 | A | * | 7/1976 | Sobeck, Jr. | ................... 132/270 |
| 5,116,388 | A | | 5/1992 | Brooks | |
| 5,146,937 | A | | 9/1992 | Lefbvre | |
| 5,771,906 | A | * | 6/1998 | De Benedictis | ............. 132/207 |
| 5,845,653 | A | | 12/1998 | Abercrombie | |
| 5,879,691 | A | | 3/1999 | Sagel et al. | |
| 5,888,249 | A | | 3/1999 | Laurila et al. | |
| 5,888,484 | A | | 3/1999 | Schmitt et al. | |
| 5,891,453 | A | | 4/1999 | Sagel et al. | |
| 5,931,168 | A | | 8/1999 | Abercrombie et al. | |
| 6,148,829 | A | * | 11/2000 | De Benedictis | ............. 132/207 |
| 6,295,993 | B1 | * | 10/2001 | Ouellette | ..................... 132/208 |
| 6,647,989 | B1 | * | 11/2003 | De Benedictis | ............. 132/210 |
| 2004/0031502 | A1 | * | 2/2004 | Winckels et al. | ........... 132/270 |
| 2004/0231689 | A1 | * | 11/2004 | Kobayashi et al. | ......... 132/222 |

* cited by examiner

FOREIGN PATENT DOCUMENTS

EP          0 945 085 A1    9/1999

*Primary Examiner*—Todd E. Manahan
(74) *Attorney, Agent, or Firm*—Vladimer Vitenberg; Marianne Dressman; Tara M. Rosnell

(57) ABSTRACT

An implement for treating strands of hair comprising a reservoir containing a composition and guide means capable of sliding in the reservoir. The guide means comprises a body extending through the reservoir, pulling means (e.g. a pull strip) protruding from one end of the reservoir for at least partially pulling the guide means out of the reservoir and attaching means (e.g. a hook) protruding from another end of the reservoir for attaching the strands of hair to said guide means. When the guide means is pulled out of the reservoir, the strands of hair to be treated are pulled in the reservoir through the first opening, and are treated by the composition therein. The implement is preferably ready-to-use.

14 Claims, 1 Drawing Sheet

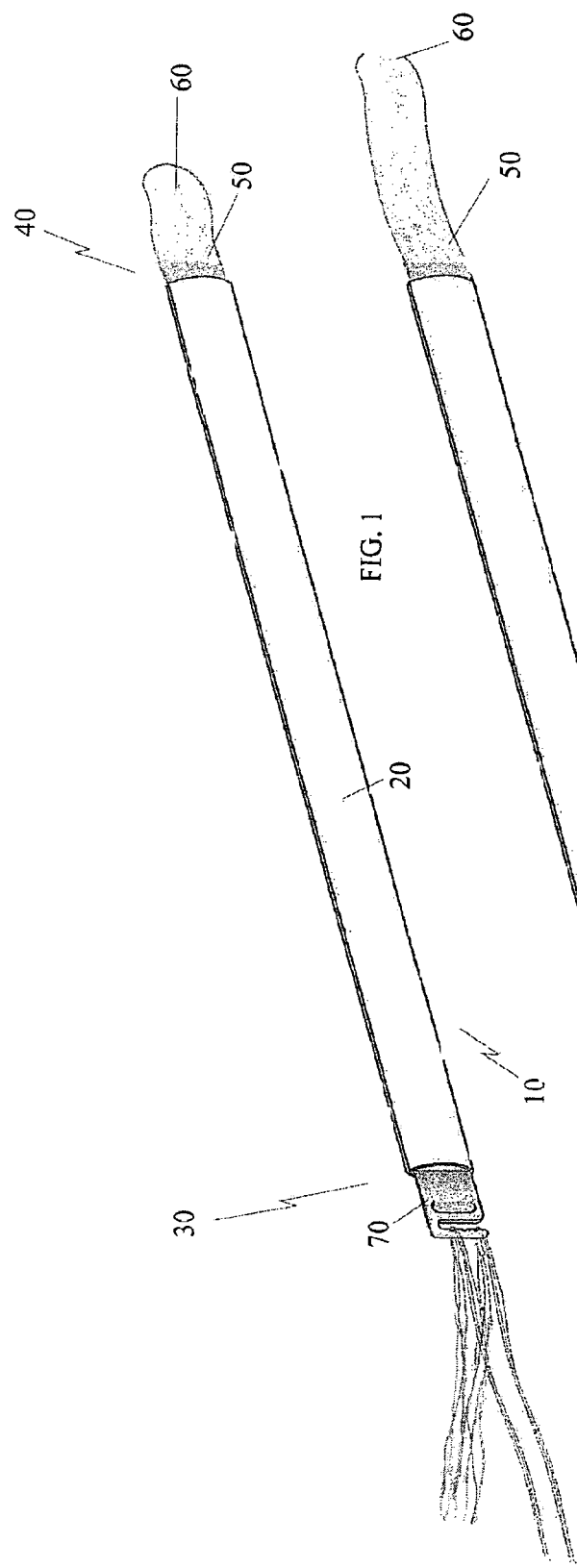
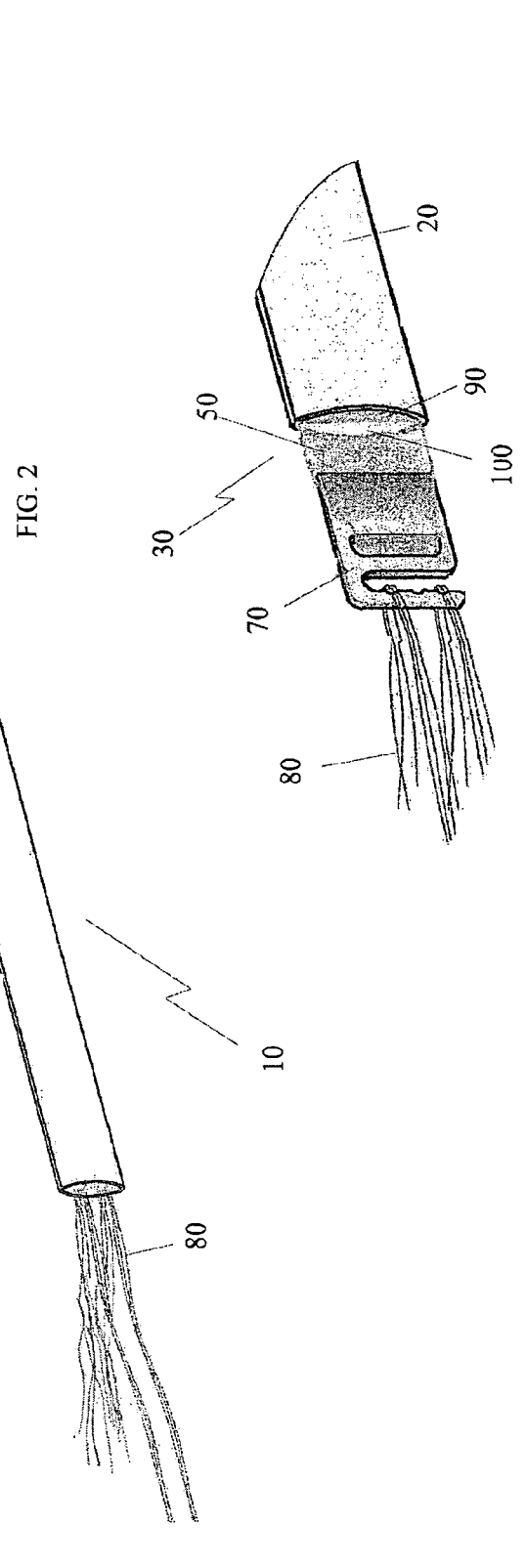

IMPLEMENT FOR TREATING HAIR AND METHOD OF TREATING HAIR USING THE SAME

BACKGROUND OF THE INVENTION

The present invention relates to an implement for the cosmetic treatment of hair, in particular hair highlighting.

Hair highlighting has been one of the mainstays of the professional salon industry. In this process, strands of hair are segregated from the remainder and treated with a composition typically comprising peroxides and/or persulfates. The technical skill required to separate the target hair and mix and apply decolorizing products to only those areas has kept this procedure mostly in the purview of hair salons. Traditionally, the segregation of hair was done by applying a plastic cap over the head and drawing small sections of hair through it. More commonly now, hair is selected through weaving and then placed onto metallic foils (usually aluminum foil) that are then painted with the highlighting composition. This allows for smaller, more independent sections to be treated, resulting in a more natural highlighted look. Although the effect is visually more appealing, these procedures are time consuming and generally require the skill of a professional haircolorist. Salons charge accordingly—often in excess of 100 USD per service.

Some highlighting services, especially on clients with lighter haircolor or those who desire less contrast in their highlights, are performed using oxidative haircolor techniques and products. These are performed using oxidative haircolor tints that have little or no oxidative dye precursors and are alkalized with relatively high levels of common hair dye alkalizers (generally, but not limited to, ammonium hydroxide and monoethanolamine). These are combined at the time of the service with high-volume peroxide developers to form an unstable highly alkalized peroxide composition that can effectively decolorize hair to a limited extent. By "high volume peroxide developer" we mean, as generally understood in the art of hairdressing, an aqueous peroxide solution, suspension, or emulsion that contains hydrogen peroxide in an amount greater than 30 volume (approximately 9.0% w/w). Higher levels of oxidative dye precursors (couplers and developers) in addition to the alkilizing agent may also be used if a further coloring effect is desired. In this case, the highlighted strands of hair will be at least partially colored by the oxidative dyes in addition to losing its natural shade due to the destruction of the natural pigments of hair (melanin) by the oxidizing agent. Therefore for the purpose of this application, the term "highlighting" encompasses "bleaching only" treatment and "bleaching plus dyeing" treatment (also referred to in the art as "permanent dyeing" or "permanent coloring").

Commonly, hair salons use high lift powdered bleaches for highlighting effects. High lift bleaches, using combinations of sodium, potassium, and ammonium persulfate along with hydrogen peroxide at elevated pH, provide fast decolorizaion with an acceptable amount of hair damage. Up to seven levels of lift are possible using a single application of some off-the-scalp bleaches. These are difficult to use due to the need to combine the persulfate mixture with the peroxide immediately prior to use. The high volume peroxide may be irritating to skin and mucous membranes. The persulfate powders are dusty and can be irritating if inhaled. This procedure is also limited by the technology in that the metallic foils need to be opened periodically to determine the degree of decoloration. Thus despite the high demand for these effects, high lift treatments are relegated to a small corner of the at-home consumer market.

Hydrogen peroxide solutions have been formulated into hair lightening products for consumer use. Products such as Sun In (RTM), A Touch of Sun (RTM), and most recently Salon Selectives Lighten Up Highlighting Mousse (RTM) have been introduced to give consumers a gradual highlighting effect. Hydrogen peroxide is unstable for storage at elevated pH (generally greater than pH 4.0) and the decolorizing effect of it at low pH is relatively weak. Therefore multiple applications of low pH products applied repeatedly over time are required to achieve a desired lightening effect. Further, these are whole-head lightening effects. Further examples of bleaching compositions are disclosed in U.S. Pat. Nos. 5,888,484 and 5,888,249.

As discussed above, highlighting usually involves mixing a first composition comprising an oxidizing agent and a second composition comprising an alkalizing agent and optionally oxidative dye precursors. The mixed composition should be carefully applied on the strands of hair to be treated so that it does not spread to adjacent sections of hair. In addition to the aluminum foil discussed above, various systems have been proposed for making sure that the composition remains on the strands of hair to be treated. For example U.S. Pat. Nos. 5,845,653 and 5,931,168 disclose applicators for transferring color-altering material from a rigid substrate to hair or fibers.

Methods have also been proposed in which the strands of hair to be colored are pulled inside a tube, which is then filled with a dye or bleach composition.

In U.S. Pat. No. 2,655,924 the strands of hair to be treated are pulled inside a tube using a hooked needle. A dyeing or bleaching composition is subsequently poured inside the tube, which is then sealed for the duration of the treatment.

U.S. Pat. No. 2,819,721 discloses another method of dyeing or bleaching hair wherein the hair to be treated is drawn in a first tube of deformable liquid-impervious material. The strands of hair are pulled inside the first tube of deformable material using a second tube movable within the first and having a jaw mechanism that can be actuated by the user. The first tube is subsequently filled with the treating composition.

U.S. Pat. No. 5,146,937 discloses the use of a sheet made of polymer material, preferably polystyrene, as a dye-applying pad for hair highlighting. The polystyrene sheet defines one and another opposite flat portions merging about a fold line. A lock of hair is laid over one flat half portion of the sheet, and a fluid dye solution including oxidizing means is applied to the lock of hair. The other flat half portion of the sheet is then folded over and flatly compressed against the first portion of sheet to take the locks in a sandwich for a sufficient development time to enable permanent hair coloring.

However, in these methods the handling of a fluid reactive composition by the consumer is required, which can be messy and may require specialist training. There is therefore a need for an implement for carrying out treatments such as hair highlighting that is ready to use, i.e. does not require the manipulation of any chemicals by the consumer.

U.S. Pat. Nos. 5,891,453 and 5,879,691 teach the use of strips of clear plastic coated with a hydrogen peroxide gel using a carbopol resin to whiten teeth.

U.S. Pat. No. 5,116,388 teaches the use of persulfate compositions enclosed in PVA packettes and their use in hair bleaching.

SUMMARY OF THE INVENTION

The present invention relates to an implement for treating strands of hair with a composition. The implement comprises:

a. a reservoir comprising a first opening and a second opening and containing a composition capable of treating hair,
b. guide means capable of sliding in said reservoir, the guide means comprising:
  i. a body extending from the first opening to the second opening through the reservoir,
  ii. pulling means protruding from the second opening for at least partially pulling the guide means out of the reservoir through the second opening,
  iii. attaching means protruding from the first opening for attaching the strands of hair to said guide means so that when the guide means is pulled out of the reservoir through the first opening the strands of hair to be treated are pulled in the reservoir through the first opening.

The implement is preferably ready-to-use.

In a preferred embodiment, the body of the guide means divides (preferably hermetically) the reservoir into two regions, wherein the first region comprises a first composition and the second region comprises a second composition different from the first. The two compositions react together to form a hair treating composition when put in contact, optionally with an activation step. When the guide means is pulled out of the reservoir through the second opening, the first and second compositions are put into contact and react to form the treating composition. At the same time, the strands of hair are pulled inside the reservoir and are placed in the position left by the guide means, resulting in the contacting of the strands of hair with the treating composition.

Also the reservoir is preferably elongated and comprises on one end the first opening and on the other end the second opening.

BRIEF DESCRIPTION OF THE DRAWINGS

FIG. 1 is a perspective view of an embodiment of the invention.

FIG. 2 is a perspective view of the embodiment of FIG. 1 wherein the guide means is partially pulled out of the reservoir.

FIG. 3 is a close-up view of a hook used in the embodiment of FIG. 1 to attach the strands of hair to the guide means.

DETAILED DESCRIPTION OF THE INVENTION

For the purpose of this invention, by "treatment of hair" or "method for treating hair" we mean as recognized by a beautician any of the common cosmetic hair treatments. The treatment may requires the mixing of two or more compositions, which compositions may chemically or physically react to form an active composition. The treatments include, but are not limited to, permanent or oxidative coloring, permanent waving, decolorizing processes such as: bleaching, highlighting, chunking, foiling etc. It will be obvious to those skilled in the art of cosmetic hair treatment that this invention has utility and advantages in other treatment modalities. The Applicant also envisions that other geometries of substrate can be used.

Throughout this description, a consumer may be any person who uses the method or the implements according to the invention. Some non-limiting examples: (a) in the case of a person who makes a personal use of the device, for example for highlighting their own hair or the hair of a friend or relative at home, the consumer is that person; (b) in the case of a person who goes to a salon or elsewhere to have a cosmetic product applied to their body by a beauty-care specialist, for example hair coloring by a hair care professional, that beauty-care specialist is the consumer; and (c) in the case of a person who dispenses a mixed product onto the coat of a pet or other animal, the consumer is that person.

Except as otherwise noted, all amounts including quantities, percentages, portions, and proportions, are understood to be modified by the word "about", and amounts are not intended to indicate significant digits. Except as otherwise noted, the articles "a", "an", and "the", mean "one or more". All documents cited are, in relevant part, incorporated herein by reference. The citation of any document is not to be construed as an admission that it is prior art with respect to the present invention.

As used herein the term "hair" to be treated may be "living" i.e. on a living body or may be "non-living" i.e. in a wig, hairpiece or other aggregation of non-living keratinous fibers. Mammalian, preferably human hair is preferred. However wool, fur and other keratin containing fibers are suitable substrates for the compositions according to the present invention.

As used herein, the term "applied" when referring to a composition is to encompass the terms coated, absorbed, adsorbed and adhered. Although the compositions are preferably applied directly to the inner wall of the reservoir without an intermediate layer, an intermediate layer such a double-sided tape may be used in some cases to facilitate the adherence of the compositions to the substrate. Preferably the implement is sold with the compositions already applied on the wall of the reservoir and "ready-to-use" by the consumer.

The term "packaged in a ready-to-use form" or "ready-to-use" as used herein means that the consumer can use the implement without having to manipulate any chemical. The implement is preferably sold with the compositions already applied on the inner wall of the reservoir and "ready-to-use".

The term "single-use" as used herein means that the implement is normally used only once before being discarded.

Essential and optional elements of the methods and implements according to the present invention will now be described in detail by reference to various exemplary embodiments of the invention, several of which are also illustrated herein, wherein like numerals indicate the same elements throughout the description.

The Implement

FIGS. 1–3 illustrate an embodiment of the implement according to the present invention, which is generally indicated as 10.

As illustrated in FIG. 1, the implement 10 of the present invention comprises a reservoir 20 comprising a first opening 30 and a second opening 40. The reservoir is preferably substantially elongated so that it conforms to the elongated shape of human hair. The distance between the first and second openings is preferably at least 5 cm, more preferably 10, even more preferably between 15 and 20 cm although longer reservoir could be used for longer hair. The reservoir may be formed in a variety of ways and from a variety of materials. A convenient way to form the reservoir is to fold a thin strip of flexible material along its longitudinal axis so as to form a reservoir having a tubular shape as illustrated on FIGS. 1–2. The reservoir may be maintained in its position by heat-sealing, applying an adhesive on the longitudinal edges of the strip of material, or the reservoir may contain a composition sufficiently sticky for the reservoir to keep its folded position.

The material making the wall of the reservoir may be formed from, but are not limited to, material such as paper, plastic, fabric, rubber, metal foil, natural or synthetic woven or nonwoven material, polymeric films such as thermoplastic films of polyethylene or polypropylene, composite materials such as a coated nonwoven or a film-coated nonwoven material or any combinations thereof. Polymeric films are preferred, for example linear low, low, medium or high density polyethylene. Polymeric films may be easily extruded or cast and die cut to conform to the desired shape and dimensions of the substrates.

The materials that may be used for the reservoir are preferably durable and disposable. They are preferably impervious to liquids and chemically compatible with the compositions used and are preferably manufactured from a thin plastic film, although other flexible liquid impervious materials may also be used. The material is preferably sufficiently flexible to be easily and safely applied to hair and sufficiently rigid to retain its overall shape during use, especially in a folded position. The substrate may thus further be described as:
- capable of supporting the composition(s) throughout storage and cosmetic application,
- impervious to liquids,
- not chemically reacting with the composition(s) prior to or during application,
- sufficiently flexible to be easily and safely applied to hair and sufficiently rigid to retain its shape during use, and/or
- capable to be formed into a continuous looped tape.

The substrates may be preferably provided as clear or translucent to allow the operator to view the progress of the chemical treatment. The substrates may also comprise a specialized indicating agent that would indicate the progress of the reaction, for example by indicating changes in pH or RA (Reserve Alkanility).

The substrates may be partially or totally made of a water-soluble material (e.g. polyvinyl alcohol) such that upon rinsing they would either dissolve or be easily removed from the strands of hair on which they were applied.

The reservoir comprises at least one composition capable of treating hair. The reservoir may also comprise two compositions capable of forming a hair treating composition when mixed. Suitable compositions will be discussed below.

The implement according to the invention further comprises guide means 50 capable of sliding in said reservoir. The guide means comprises a body 50 extending through the reservoir and connecting the first opening to the second opening. As shown in FIGS. 1–3 the body 50 may be in the form of a strip of material dividing (preferably hermetically) the reservoir into two separate regions. The body may be formed from a material selected from paper, plastic, fabric, rubber, metal foil, natural or synthetic woven or nonwoven material, polymeric films such as thermoplastic films of polyethylene or polypropylene, composite materials such as a coated nonwoven or a film-coated nonwoven material, or any combinations thereof. The regions of reservoir divided by the body 50 are preferably substantially symmetrical and have substantially the same volume. The first region may be filled with a composition different from the composition filling the second region, as will be discussed below.

The guide means further comprises pulling means 60 protruding from the second opening of the reservoir for at least partially pulling the guide means out of the reservoir through said second opening. As shown of FIG. 1, the pulling means may be in the form of strip of material, often referred to in the art as "pull-strip". The body and the pulling means may be made of the same material or a different material. For example, the pull-strip of FIG. 1 could be an extension of the body 50 on which a further layer of reinforcing material such as paper would have been adhered to. "Pull-strip" systems are now commonly found in everyday-use package and will be intuitively used by a consumer. A further layer may include instructions, in the forms of words or drawings (such as an arrow) printed on it so as to further reinforce the consumer's intuition.

The guide means further comprises attaching means 70 protruding from the first opening for attached the strands of hair 80 to the guide means. When the consumer pulls the guide means out of the reservoir, the strands of hair to be treated which are attached to the guide means are pulled in the reservoir through said first opening. As shown on FIG. 3, the attaching means may be in the form of hook. The material used for the attaching means should preferably be sufficiently rigid to keep its shape when pulled in the reservoir. More elaborated attaching means may be devised, for example hooks allowing the hair to be weaved. It should be noted than in FIGS. 1 and 2 only a fraction of the hair attached to the hook is represented. In order to make reduce the ability of the strands of hair to slide around the hook when it is pulled in the consumer may hold the strands of hair to be treated in a tight loop while the hook is pulled in the reservoir. With this hook, the maximum length of the hair that may be treated is twice as the length of the reservoir.

FIG. 2 illustrates the implement 10 in an intermediate position wherein the guide means has been partially pulled out of the reservoir 20. Accordingly, the hook 70 has been simultaneously pulled in the reservoir for the same distance, carrying with it a section of the hair to be treated. The hook may be pulled in the reservoir even further, the limit being the length of the reservoir or the length of the hair that is pulled in. If the hair is sufficiently long, the hook may be pulled out of the reservoir through the second opening, and optionally removed form the hair to which it is attached while the treatment of the hair take place in the reservoir.

The reservoir may comprise one composition capable of treating hair. In the case of a reservoir comprising a single composition, suitable compositions that may be used include dyes (e.g. direct dyes or semi-permanent dyes) or conditioners. Preferably the reservoir comprises two compositions 90, 100 in two regions of the reservoir hermetically divided by the guide means, as illustrated in FIG. 3. When the guide means is pulled outside of the reservoir, the strands of hair take the place of the guide means and are sandwiched between the first and second compositions. In addition to these first and second compositions, said regions may comprise additional compositions. For example, if the treatment is a highlighting treatment with a dye component, it would be possible to have a dye composition and a peroxide composition regularly and alternatively applied in each region of the reservoir along the guide means, said guide means separating the dye composition on one side and said peroxide composition on the other side. It would also be possible to have several dye compositions in one region of the reservoir and a peroxide composition in the other section of the reservoir. In this configuration the different dye compositions may applied as adjacent stripes along the axis defined by the guide means. These two configurations are not necessarily limited to dye and peroxide compositions.

The following will describe some of the compositions that may be used in combination in the case of an implement comprising two different compositions that react (e.g.g physically or chemically) together once brought in contact to form a hair treating composition. When the first and second compositions are brought into contact, the hair treating composition may be formed immediately or a further activation step may be required.

For example the reaction may be heat-, water- or pressure-activated. In the case of water-activation, the hair could be wetted prior to being placed between the substrates or the substrates could be wetted prior to being applied on the strands of hair, or both. In a further, alternate, embodiment, an activation step may be required in order to bring the first and second compositions in contact with other. For example, pressure-activation may take place if the compositions are trapped in plastic bubbles that are easily frangible, such as polyethylene or polypropylene "CARMA" bubbles, supported by a backing made of a plastic material. "CARMA" stands for "Consumer Activated Rupturable Multi-cell Applicators", a film technology for delivering product to a surface, consisting of product trapped in closed cells, which when ruptured deliver the trapped product to the surface. The bubbles would be burst, and the products that they contain released, by applying a sufficient amount of pressure on the outer surfaces of the substrates. The compositions contained in the bubbles would then mix, permitting them to form the treating composition.

The amount of substance applied on the substrates will depend upon the size and capacity of the piece of material, concentration of the actives, and the desired end results.

In a preferred embodiment, the hair treating composition formed by the first and second compositions will be a composition suitable for highlighting hair, optionally comprising oxidative dye precursors for coloring the hair.

The compositions according to the present invention can be provided in any form for highlighting hair and/or coloring hair, such as an aqueous composition, a paste, a viscous liquid, a powder, a gel or an oil-in-water emulsion. Preferred media for the compositions according to the present invention are thickened solutions comprising a salt-tolerant thickener or oil-in-water emulsions. Preferably the compositions applied on the substrates are in the form of a gel, which provides good adhering properties to the products and a source of water that may facilitate the mixing of the reactants comprised in the first and second compositions. Hydrogels are especially preferred.

The compositions may also comprise a water-soluble material that would dissolve upon rinsing (e.g. PVA), thus facilitating the release of the implements when the treatment is finished.

EXAMPLES OF COMPOSITIONS

The following are examples of compositions that may be used as first and second compositions in the case of an implement comprising two different compositions. It is unimportant which is designated as first composition and which is designated as second composition.

Example 1

Hydrogen Peroxide Composition

An exemplary hydrogen peroxide composition that may be applied on the first or second substrates may comprise the following:
1. Water, typically 5–95%,
2. Thickening agent, typically 0.1–20%,
   Preferred thickening agents are chosen from polymers (including gelling agents), gel phases referred to as creams or emulsions and combinations thereof.

Suitable polymers may be selected from carboxymethyl cellulose, carboxypropyl cellulose, carboxypolymethylene (Carbomers, Carbopols e.g. Carbopol ETD 2020, all RTM), carboxyvinyl Polymers, poloxamers, polyethylene glycol, natural gums (including but not limited to carrageenan, tragacanth, karaya, arabic, guar and xanthan), natural and synthetic smectite clays (including but not limited to hectorites, bentonites and montmorillonites), scleroglucan, methyl cellulose, ethyl cellulose (connmercially available as Aquacote (RTM)), hydroxyethyl cellulose (Natrosol, hydroxypropylmethyl cellulose, microcrystalline cellulose, hydroxybutylmethyl cellulose, hydroxypropyl cellulose (Klucel (RTM)), hydroxyethyl ethyl cellulose, cetyl hydroxyethyl cellulose (Natrosol (RTM) Plus 330), N-vinylpyrollidone (Povidone (RTM)), Acrylates/Ceteth-20 Itaconate Copolymer (Structure (RTM) 3001), hydroxypropyl starch phosphate (Structure (RTM) ZEA), polyethoxylated urethanes or polycarbamyl polyglycol ester (e.g. PEG-150/Decyl/SMDI copolymer=Aculyn (RTM) 44, PEG-150/Stearyl/SMDI copolymer=Aculyn 46 (RTM) ), trihydroxystearin (Thixcin (RTM)) acrylates copolymer (e.g. Aculyn (RTM) 33) or hydrophobically modified acrylate copolymers (e.g. Acrylates/Steareth-20 Methacrylate Copolymer=Aculyn (RTM) 22).

A representative but not exhaustive list of polymers and thickening agents can be found in "The Encyclopaedia of Polymers and Thickeners for Cosmetics" compiled and edited by Robert Y. Lochhead, phD and William R. Fron, Department of Polymer Science, University of Southern Mississippi Suitable gel phase referred to as creams or emulsions may be selected from cetyl alcohol, stearyl alcohol, fatty acids and mixtures thereof.

3. Hydrous peroxide compound, typically 0.1–35%,

For example cosmetically acceptable peroxide producing compounds, including but not limited to: peroxides (hydrogen, calcium, carbonates (e.g. sodium, ammonium, potassium), carbamides, alkaline earth, inorganic alkali metal peroxides (e.g. sodium periodate, sodium peroxide), organic peroxides (e.g. urea peroxide, melamine peroxide), inorganic perhydrate salt bleaching compounds (e.g. alkali metal salts of perborates, percarbonates, perphosphates, persilicates, persulphates) etc.

4. Optionally glycerine, typically 1–50%.

The composition is preferably in the form of a gel.

Example 2

Peroxygen Generator Blend

An exemplary peroxygen generator blend composition that may be applied on the first or second substrates may comprise the following:

1. Peracid compound, typically 1–60%.

Suitable peracid compounds may be persulfates (e.g. ammonium, potassium and/or sodium salts), percarbonates (e.g. ammonium, potassium and/or sodium salts), carbonates (e.g. ammonium, potassium and/or sodium salts), perhydrates (e.g. citric acid, sodium phosphate and/or sodium carbonate salts) and mixtures thereof.

2. Hydroxides (e.g. ammonium, potassium and/or sodium salts), typically 0.1–8%

3. Silicates: sodium, sodium meta-, typically 0.1–20%,

4. Surfactant: sodium lauryl sulfate (Dry Powder), typically 0.1–5.0%,

5. Silica, q.s.

Example 3

Alkalizing Composition
1. Water, typically 5–99%,
2. Thickening agent, typically 0.5–20%, Preferred thickening systems are chosen from the same list as already discussed for the hydrogen peroxide composition.

3. Cosmetic Alkalizer, typically 0.1–20%

Preferred are any or combinations of the common alkalizing agents used in cosmetic manufacture, including but not limited to hydroxides (e.g. ammonium, potassium and/or sodium salts), ethanolamines (e.g. mono-, di- and/or tri-), isopropanolamines, aminomethulpropanol, carbonates (e.g. sodium, ammonium, potassium), 4. optionally dyes, including oxidative dye precursors or direct dye.

The alkalizing composition is preferably in the form of a gel.

Other Ingredients

Moreover, it is also intended that the compositions of the present invention may comprise other components that may or may not be active ingredients. This includes, but is not limited to, additional colorants (temporary, semi-permanent, demi-permanent, or permanent and also either natural or synthetic), chelants (e.g. ethylene diaminedissucinnic acid) buffering agents, thickeners, solvents, enzymes, anionic, non ionic, amphoteric and/or cationic surfactants, conditioning agents, carriers, antioxidants, stabilizers, perming actives, perfume, hair swelling agents, hair straightening agents. Some of these additional components are detailed hereafter.

Oxidative Dye Precursors

These compounds include aromatic diamines, aminophenols and their derivatives (a representative but not exhaustive list of oxidation dye precursor can be found in Sagarin, "Cosmetic Science and Technology", "Interscience, Special Edn. Vol. 2 pages 308 to 310). Precursors can be used with couplers. Couplers are generally colorless molecules that can form colors in the presence of activated precursors.

The choice of precursors and couplers will be determined by the color, shade and intensity of coloration that is desired. The precursors and couplers can be used herein, singly or in combination, to provide dyes having a variety of shades.

The hair dye component of a hair dye compositions will generally comprise from 0.001% to 10%, preferably from 0.1% to 3%, of oxidative dye precursors and couplers.

Conditioning Agent

The compositions of the present invention preferably, but not necessarily, further comprise at least one conditioning agent. Preferred conditioning agents are selected from silicone materials, especially nonvolatile silicone and amino functionalised silicones, cationic surfactants, cationic polymers and mixtures thereof.

The conditioning agent will generally be used at levels of from 0.05% to 20% by weight of the composition, preferably of from 0.1% to 15%, more preferably of from 0.2% to 10%, even more preferably of from 0.2% to 2%. The minimum level that is used in a particular composition should be effective to provide a conditioning benefit. The maximum level that can be used is not limited by theory, but rather by practicality. It is generally unnecessary and expensive to use levels in excess of about 20%.

Suitable conditioning agents are disclosed in WO9804237 p. 22–p. 29, and in WO9632919 p. 17–22.

EXAMPLES OF HIGHLIGHTING PROCESS

Three highlighting processes are described—two using a hydrogen peroxide composition and an alkalizing gel, the last using a hydrogen peroxide composition and mixed persulfates.

Example A

Hair Decolorizing Using Gelled Peroxide and Gelled Alkalizer

A decolorizing composition that is useful for a hair highlighting consumer who desires only a small amount of lift (decolorizing) would not require the powerful peracid chemicals. This example teaches the production of a hair highlighter using gels of peroxide and a suitable cosmetic alkalizer. The compositions of example A are as follows:

| Ingredients | % w/w |
| --- | --- |
| Composition 1 - Peroxide Gel | |
| De-ionized Water | q.s. to 100% |
| Glycerine | 5.00 |
| Hydrogen Peroxide (50% Active) | 12.50 |
| Carbomer | 0.60 |
| Sodium Hydroxide (45% aq. Solution) | q.s. to pH 5.0 |
| Composition 2 - Alkalizer Gel | |
| De-ionized Water | q.s. to 100% |
| Ammonium Hydroxide (45% Active) | 4.00 |
| Carbomer | 0.25 |

The first composition may be produced by combining the carbomer with the glycerine and mixing until a homogenous slurry is obtained. De-ionized water is charged into a separate container of sufficient size to contain the entire batch. The slurry is introduced into the water slowly and mixed with moderate agitation until a stable, homogenous gel is observed. Hydrogen peroxide is then added with moderate mixing so as not to introduce excess air bubbles into the system. Then, sodium hydroxide is added dropwise to increase the pH to approximately 5.0—activating and gelling the carbomer. Optionally, additional peroxide stabilizers such as sodium stannate may be added to further reduce the likelihood of premature peroxide decomposition.

The second composition may be produced by hydrating the carbomer in rapidly mixing water—either by slow manual addition (so as not to produce "fisheyes" of undispersed polymer)—or by using an eductor or similar device for rapid hydration of powders. When the carbomer is fully dispersed and homogenous add the Ammonium Hydroxide with moderate mixing so as to avoid entrapping excess air bubbles. The batch will thicken and clear with the addition of the alkalizer.

A clear polyethylene film substrate approximately 20 long by 8 cm wide may be divided in half and folded so as to make a double sheet 4 cm wide. A layer of composition 1 approximately 0.4 mm thick is applied to one half of a clear polyethylene film. Opposite of that, book style, a layer of composition 2 of similar thickness is applied to an inside surface the polyethylene film. A guide means of similar proportion and represented in the Figures is placed between the treated halves of the film. The chemically treated halves of the strip are compressed together around the guide means.

The two sheets are heat-sealed along the longitudinal axis to hold the sheets together in a folded position. An adhesive may also be applied.

Example B

Gelled Peroxide and Gelled Alkilizer Comprising Oxidative Dye Precursors

A second preferred method of this invention may be to use a divided substrate treated on one side with a hydrogen peroxide gel and on the other side with an alkaline gel containing oxidative dye precursors. In this example the simultaneous bleaching of the underlying substrate colour and deposition of dyes will result in a mid brown shade.

The compositions of example B are as follows:

| Ingredients | % w/w |
|---|---|
| Composition 1 - Peroxide Gel | |
| De-ionized Water | q.s. to 100% |
| Glycerine | 5.00 |
| Hydrogen Peroxide (50% Active) | 12.50 |
| Disodium EDTA | 0.04 |
| Carbomer | 0.60 |
| Sodium Hydroxide (45% aq. Solution) | q.s. to pH 5.0 |
| Composition 2 - Oxidative Dye + Alkalizer Gel | |
| De-ionized Water | q.s. to 100% |
| Ammonium Hydroxide (45% Active) | 4.00 |
| Carbomer | 1.00 |
| Glycerine | 5.00 |
| Sodium Sulphite | 0.10 |
| EDTA | 0.05 |
| Erythorbic acid | 0.40 |
| Para-phenylenediamine | 0.76 |
| Citric Acid | 0.40 |
| N,N-Bis(2-Hydroxyethyl)-P-Phenylenediamine | 0.41 |
| Resorcinol | 0.40 |
| 1-Napthol | 0.01 |
| m-aminophenol | 0.02 |
| Phenyl Methyl Pyrazolone | 0.10 |
| Toluene-2,5-diamine Sulphate | 0.076 |
| Trisodium Ethylenediamine Disuccinate | 6.7 |

The first composition is produced by combining the carbomer with the glycerine and mixing until a homogenous slurry is obtained. De-ionized water is charged into a separate container of sufficient size to contain the entire batch. The slurry is introduced into the water slowly and mixed with moderate agitation until a stable, homogenous gel is observed. Hydrogen peroxide is then added with moderate mixing so as not to introduce excess air bubbles into the system. Finally sodium hydroxide is added dropwise to increase the pH to approximately 5.0—activating and gelling the carbomer. Optionally, additional peroxide stabilizers such as sodium stannate may be added to further reduce the likelihood of premature peroxide decomposition.

The second composition is produced by hydrating the carbomer in rapidly mixing water—either by slow manual addition (so as not to produce "fisheyes" of undispersed polymer)—or by using an eductor or similar device for rapid hydration of powders. When the carbomer is fully dispersed and homogenous add all the remaining ingredients, apart from ammonium hydroxide (i.e. glycerine, dye precursors, pH buffers and antioxidants). Once they have dissolved, the ammonium hydroxide is added with moderate mixing so as to avoid entrapping excess air bubbles. The batch will thicken and clear with the addition of the alkalizer.

The implement is then prepared as in example A.

Example C

Hair Decolorizing Using Persulfates and Peroxide

A third preferred method of this invention is to use a divided substrate treated on one side with a persulfate bleach mixture similar to the professional salon product Basic White Dedusted Highlighting Bleach (RTM) opposite a concentrated hydrogen peroxide gel. This may provide a high level of decolorizing effect in a short amount of time and with an acceptable degree of hair damage. As persulfate bleaches are typically sold in the form of a blended anhydrous powder, a method of immobilizing the powder mixture may be required. Hydrogen peroxide, a cosmetic oxidizer, maybe sold as a water-thin liquid solution and may be immobilized for use within the scope of the invention.

Powdered compositions of persulfates may be more difficult to immobilize. Although soluble in water, persulfates typically decompose rapidly and exothermically upon hydration. Therefore conventional aqueous gelling agents are typically not suitable for use. Anhydrous slurries, pastes and creams of persulfates in oils, waxes and/or silicones do exist (see Wella patent below), but may be less desirable for use in this invention, unless their hydrophobic nature is overcome. These typically do not readily mix with gelled peroxide upon simple contact. Decolorant slurries adsorbed within a textile as described in U.S. Pat. No. 5,888,249 provide a method to immobilize ammonium carbonate, but have not been proven to work with the preferred persulfates.

A method of persulfate immobilization described in U.S. Pat No. 5,116,388 is to package the powder in small pockets of polyvinyl alcohol (PVA) films, adhered to a plastic substrate. In this way a measured dose of persulfate composition can be safely and cleanly adsorbed onto the supporting substrate and remain separated from the peroxide composition. Such PVA films are readily soluble in the peroxide gel. Upon contact with the peroxide gel, the PVA dissolves and the persulfate blend mixes with the peroxide gel to for the decolorizing composition. To further enhance the mixing, a small amount of a salt, preferably sodium chloride, can be added to either the persulfate mixture or applied to the exterior surface of the PVA film. Upon contact with the salt, the peroxide gel will typically quickly lower in viscosity and more readily flow into and mix with the persulfate blend.

The Compositions of Example C are as Follows:

| Ingredients | % w/w |
|---|---|
| Composition 1 - Peroxide Gel | |
| De-ionized Water | q.s. to 100% |
| Glycerine | 5.00 |
| Hydrogen Peroxide (50% Active) | 12.50 |
| Carbomer | 0.60 |
| Sodium Hydroxide (45% aq. Solution) | q.s. to pH 5.0 |
| Composition 2 - Peroxygen Generator Blend | |
| Silica | q.s. to 100% |
| Ammonium Persulfate | 20.0 |
| Potassium Persulfate | 35 |
| Sodium Persulfate | 5.0 |
| Sodium Metasilicate | 10.0 |
| Sodium Lauryl Sulfate | 1.0 |
| Sodium Chloride | 0.25 |

The first composition may be produced by combining the carbomer with the glycerine and mixing until a homogenous slurry is obtained. De-ionized water is charged into a separate container of sufficient size to contain the entire batch. The slurry is introduced into the water slowly and mixed with moderate agitation until a stable, homogenous gel is observed. Hydrogen peroxide is then added with moderate mixing so as not to introduce excess air bubbles into the system. Then, sodium hydroxide is added dropwise to increase the pH to approximately 5.0—activating and gelling the carbomer. Optionally, additional peroxide stabilizers such as sodium stannate may be added to further reduce the likelihood of premature peroxide decomposition.

The second composition is produced by the dry blending of all of the dry ingredients, in any order, in a suitable blending apparatus such as a V-blender. The composition should be combined to homogeneity by whatever blending means are chosen.

Approximately 5 grams of the blended persulfate composition is then poured into a 10 cm by 3 cm packet made of dried PVA polymer films. This is heat sealed so as to exclude moisture until the time of use. The packet is adhered to one side of the divided support substrate using double-sided transparent adhesive tape. The peroxide gel of composition 1 is applied to the opposing side of the support substrate in the same manner as the previous example.

The implement is then prepared as in example A.

OTHER ADVANTAGES AND VARIATIONS OF THE PRESENT INVENTION

The method and implements according to the present invention may be used in combination with an all-over treatment of the hair. For example, a previous hair treating composition (e.g. hair coloring) could previously be applied to the whole of the hair and then followed by the applications of the implements of the present invention. This would have the advantage of, at the same time, giving grey coverage or changing the color of the rest of the hair whilst highlighting selected strands of hair. Alternatively, the implements could be previously applied to strands of hair and while still on the head, a further treating composition (coloring) could be applied to the remainder of hair, with the same advantages as above.

The implements can be sold separately or in a package comprising several implements. In the latter cases, the implements can all be the same (same treating composition), or different (for example to achieve different type of color highlight). The implements may be packaged individually in a sealed package.

The implements could also be sold in bulk rolls for the professional market from which sections would be cut according to length or width of hair to be treated.

All documents cited in the Detailed Description of the Invention are, in relevant part, incorporated herein by reference; the citation of any document is not to be construed as an admission that it is prior art with respect to the present invention.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

The invention claimed is:

1. An implement for treating selected strands of hair with a composition, said implement comprising:
 a) a reservoir comprising a first opening and a second opening and containing a composition capable of treating hair, the reservoir comprising an elongated tubular shape having a longitudinal axis and formed of a material sufficient to retain the elongated tubular shape during use:
 b) guide means capable of sliding in said reservoir, wherein said guide means comprises:
  (i) a body extending from said first opening to said second opening through the reservoir;
  (ii) pulling means protruding from said second opening for pulling said guide means at least partially out of the reservoir through said second opening;
  (iii) rigid attaching means protruding from the first opening for attaching the selected strands of hair to said guide means so that when said guide means is pulled out of the reservoir through said second opening the strands of hair are pulled in the reservoir through said first opening.

2. An implement according to claim 1 wherein said reservoir is formed by a strip of material folded along its longitudinal axis.

3. An implement according to claim 2 wherein said reservoir is maintained in a folded shape by heat-sealing.

4. An implement according to claim 2 wherein said reservoir is maintained in a folded shape by an adhesive.

5. An implement according to claim 1 wherein said material is polyethylene.

6. An implement according to claim 1 wherein said body of said guide means is an inner strip of material, said pulling means is a pull strip extending outside the first opening and attached to one end of said inner strip, and said attaching means is a hook attached to the other end of said inner strip.

7. A method for treating strands of hair comprising the subsequent steps of:
 a) providing an implement according to claim 1;
 b) attaching the strands of hair to be treated to the attaching means;
 c) using the pulling means such that the body is pulled out of the reservoir for the stands of hair to be sufficiently enclosed in the reservoir;
 d) leaving the strands of hair to be treated inside the reservoir for the duration of treatment;
 e) removing the strands of hair from the reservoir.

8. A method according to claim 7 further comprising the step of rinsing the strands of hair.

9. An implement for treating selected strands of hair with a composition, said implement comprising:
 a) a reservoir comprising a first opening and a second opening and containing a composition capable of treating hair;
 b) guide means capable of sliding in said reservoir, wherein said guide means comprises:
  i) a body extending from said first opening to said second opening through the reservoir;
  ii) pulling means protruding from said second opening for pulling said guide means at least partially out of the reservoir through said second opening;
  iii) attaching means protruding from the first opening for attaching the selected strands of hair to said guide means so that when said guide means is pulled out of the reservoir through said second opening the strands of hair are pulled in the reservoir through said first opening; and wherein said body of said guide means divides said reservoir into two regions, wherein said first region contains a first composition and said second region contains a second composition to form a hair treating composition and wherein when said body is pulled through said second opening said first and second compositions are brought into contact.

10. An implement according to claim 9 wherein the second region contains an additional composition substantially the same as the first composition and the first region contains an additional composition substantially the same as the second composition.

11. An implement according to claim 10 wherein the compositions contained in the first region are applied on the inner surface of the first substrate according to an alternating pattern and the compositions applied in the second regions are applied complimentarily.

12. An implement according to claim 9 wherein the first region comprises at least one additional composition and wherein said at least one additional composition is also capable of reacting with the second composition to form at least one additional hair treating composition.

13. An implement according to claim 12 wherein said first composition and said at least one additional composition comprises an alkalizing agent and said second composition comprises an oxidizing agent, and wherein said hair treating composition and said additional hair treating composition are hair highlighting compositions.

14. A composition according to claim 13 wherein said first composition and said at least one additional composition further comprise oxidative dye precursors.

* * * * *